United States Patent [19]

Crowder et al.

[11] Patent Number: 4,834,443
[45] Date of Patent: May 30, 1989

[54] ROBOTIC GRIPPING DEVICE HAVING LINKAGE ACTUATED FINGER SECTIONS

[75] Inventors: Richard M. Crowder, Ramsey; David R. Whatley, Eastleigh, both of England

[73] Assignee: The Secretary of State for Defence in Her Britannic Majesty's Government of the United Kingdom of Great Britain and Northern Ireland, London, England

[21] Appl. No.: 122,732

[22] Filed: Nov. 18, 1987

[30] Foreign Application Priority Data

Nov. 19, 1986 [GB] United Kingdom ............... 8627628

[51] Int. Cl.⁴ .......................... B66C 1/28; B25J 15/12
[52] U.S. Cl. ..................... 294/106; 901/38; 901/39
[58] Field of Search ............... 294/106, 111, 112, 115; 901/31, 32, 36, 37, 38, 39; 623/63, 64, 65

[56] References Cited

U.S. PATENT DOCUMENTS

| | | | |
|---|---|---|---|
| 2,464,577 | 3/1949 | Hobbs | 623/63 |
| 3,694,021 | 9/1972 | Mullen | 294/106 |
| 4,094,016 | 6/1978 | Eroyan | 623/63 X |
| 4,246,661 | 1/1981 | Pinson | 901/36 X |

FOREIGN PATENT DOCUMENTS

| | | | |
|---|---|---|---|
| 2925225 | 1/1981 | Fed. Rep. of Germany | 901/36 |
| 615925 | 6/1978 | U.S.S.R. | 901/38 |
| 677908 | 8/1979 | U.S.S.R. | 294/106 |

Primary Examiner—Dennis H. Pedder
Assistant Examiner—Gary C. Hoge
Attorney, Agent, or Firm—William R. Hinds

[57] ABSTRACT

A gripping device which simulates the action of a human finger comprises three pivotted sections 3, 5, 7 having the middle section 5 linked to the tip section 7 by a bar 9 so that its rotation causes rotation of the tip section. Rotation of the lower section 3 is preferentially effected by a motor 11 via a sliding cross-head 15, an equalizer bar 18 and a rod 19. If this rotation is stopped by an object 25 to be gripped, the drive transfers via rod 20, crank 21 and rod 23 to the middle section 5, causing the middle and tip sections to rotate and grip the object against the lower portion as shown at 26. A robotic hand comprising four such fingers and a thumb is usable as a substitute for a human hand in a glove-box glove.

9 Claims, 3 Drawing Sheets

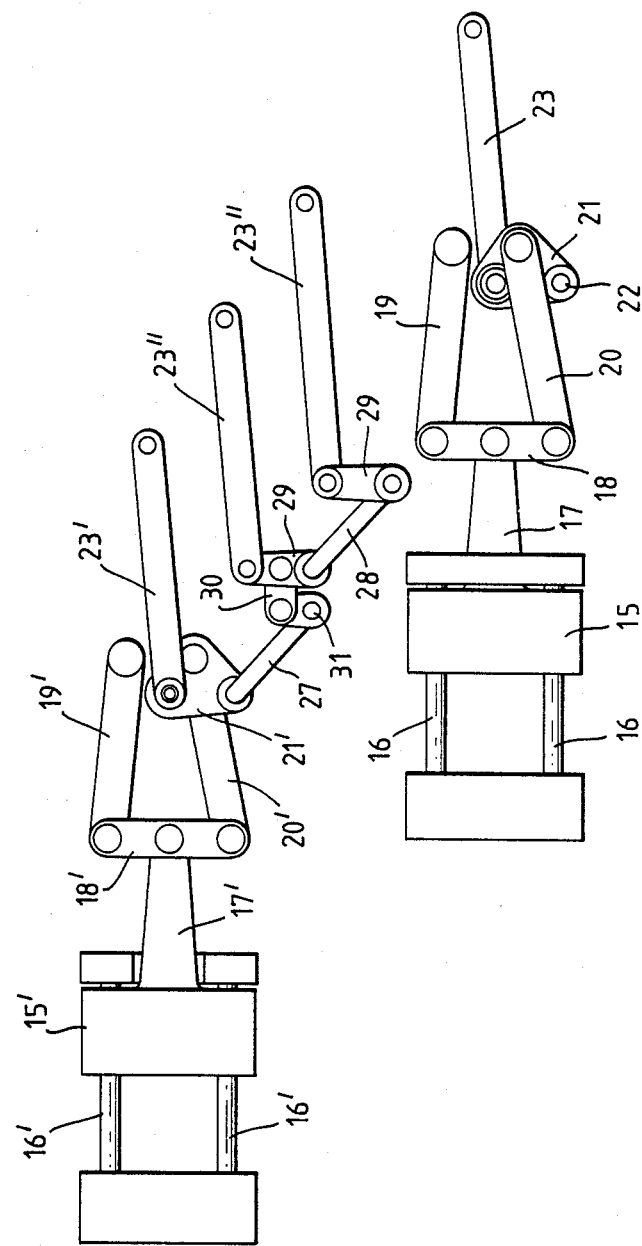

ROBOTIC GRIPPING DEVICE HAVING LINKAGE ACTUATED FINGER SECTIONS

This invention relates to gripping devices and in one form provides a device which closely simulates the action of a human finger. It has one application in providing a robotic hand as a substitute for a human hand in a glove of a glove-box for handling dangerous, particularly radioactive, materials or equipment.

In a known form of robotic hand the fingers are operated by cables. Such a hand is described, for example, by S C Jacobson et al in a paper "Design of the UTAH/MIT dextrous hand", delivered at the IEEE Conference on Robotics and Automation, San Francisco, April 1986. Cable operation is bulky, which restricts the movement of the manipulator of which the hand is part as regards both speed and spatial range thereof; it also makes insertion in a glove impractical. Additionally, there are problems peculiar to cable operation, such as cable stretch and end-connectors. The present invention does not use cables and so does not have the above disadvantages.

In a prosthetic hand described earlier by D Jakšić in a paper "Mechanics of the Belgrade Hand" (Proc. 3rd Int. Symp. on External Controls of Human Extremities, Dbrovnik, 25–30 August 1969, pp 145–149), the fingers are operated by a lever system. However, this system does not allow the action of a human finger to be simulated, as in the present invention.

According to the present invention a gripping device comprises:

a lower finger-section pivotted at its lower end to a base and at least a first upper finger-section pivotted to the lower section;

a driving means mounted on said base;

and a linkage between said driving means and said finger-sections for preferentially rotating said lower section about its pivot, said linkage being arranged so that, upon rotation of said lower section being stopped or strongly resisted by an object to be gripped, the drive transfers to said first upper section causing it to rotate about its pivot towards the lower section and thereby tend to grip the object between said finger-sections.

The linkage may comprise an equaliser bar having an intermediate point linearly moveable by said driving means and having a first rod linking one end of the bar to the lower finger-section and a second rod linking the other end of the bar to a crank pivotted on said base, said crank being linked to the first upper finger-section by a third rod, the linkage geometry, primarily, being such that the mechanical advantage obtained via the second rod is substantially less than that obtained via the first rod whereby to cause said initial preferential rotation of the lower finger-section.

In a form closely simulating the action of a human finger there is provided a second upper finger-section pivotted to said first upper finger-section and a linkage between said first and second upper finger-sections whereby rotation of said first about its pivot causes rotation of said second about its pivot.

A robotic hand may comprise four devices as defined in the immediately preceding paragraph pivotted to a common base and simulating the action of the four human fingers. In one form of hand the index finger comprises a gripping device as aforesaid operable via one said linkage by one said driving means and the other three fingers coupled together to be operable simultaneously, but independently of the index finger, via a second said linkage by a second said driving means.

The driving means may be a rotary electric motor or motors.

The invention will now be described by way of example with reference to the accompanying drawings wherein:

FIG. 3 is an expanded view of the finger-operating mechanism is the hand of FIGS. 1 and 2.

Figure 1:
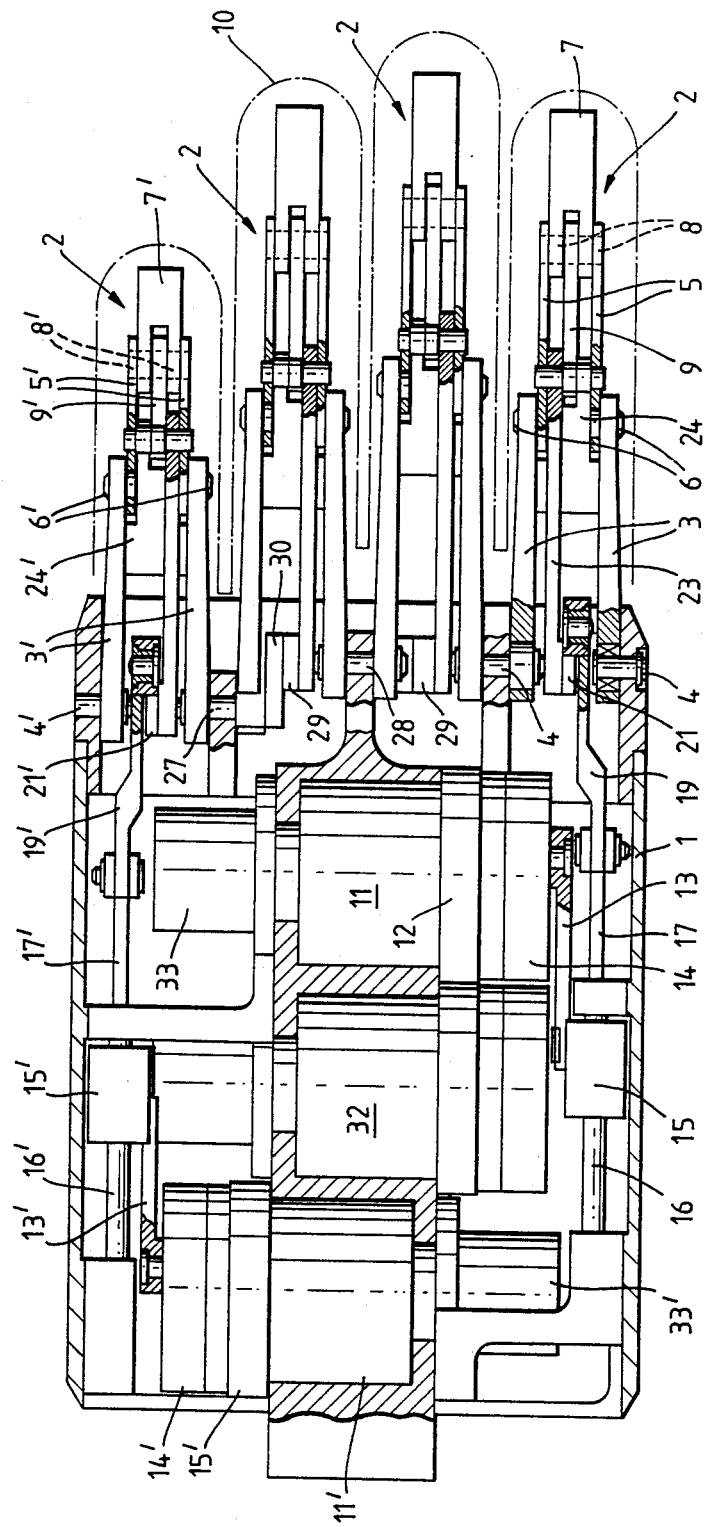
FIG. 1 is a plan view of a robotic "hand" embodying the invention "palm" side upward and with the "index finger" lowermost.
Figure 2:
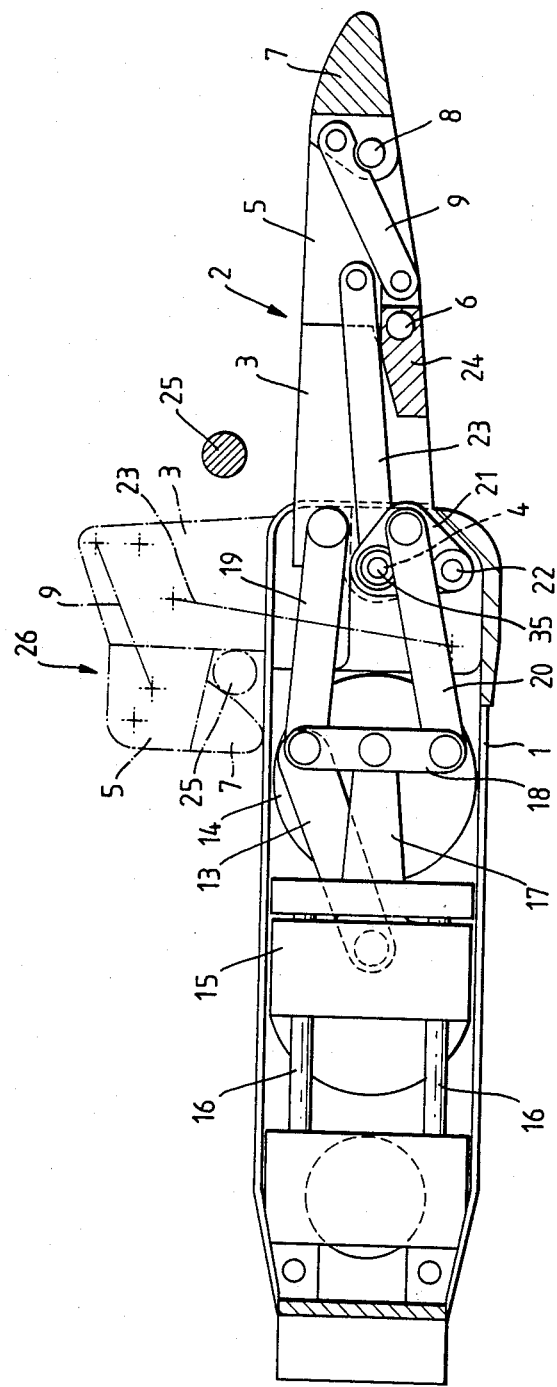
FIG. 2 is a sectional elevation of the hand of FIG. 1 taken along the index finger.

In FIGS. 1 and 2 the hand comprises a base 1 approximating to the palm of a human hand. Four fingers 2 each comprise three sections. The lower sections each comprise two parallel plates 3 which are pivotted to the base 1 at 4 (hidden in FIG. 2). The first upper (or middle) sections each comprise two parallel plates 5 which are pivotted to the respective plates 3 at 6, sandwiching a block 24 secured to the ends of the plates 3. The second upper (or tip) sections each comprise a forked member 7 pivotted to the respective plates 5 at 8. (The pivot 4 is hidden in FIG. 2 behind a crank 21). Each member 7 is linked to the respective plates 5 by a rod 9, pivotted at each end in such a way that upward rotation of the plates 5 about the pivots 4, ie, towards the palm of the hand, causes the member 7 to rotate simultaneously towards the palm about the pivots 8.

The line 10 indicates the outline of the fingers of a glove of a conventional glove-box with the present hand inserted therein.

Mounted on the base 1 is a small brushless DC motor 11 (as made by Kollmorgan Corp, USA, and marketed in the UK by Hightech Ltd) coupled to an elliptical-drive reduction gearbox 12 (as supplied by Harmonic Drives Ltd, Horsham, West Sussex). A 360 pulse/revolution incremental optical encoder 33 is fitted to the motor 11; this provides motor-position feedback for the hand control system (not shown). A connecting rod 13 links a pin on a disc 14 mounted on the output shaft of the gearbox to a pin on a cross-head 15 which slides on two parallel rods 16 using linear bearings; see also FIG. 3.

A rod 17 projects rigidly from the cross-head 15 and is connected to a pin midway (in this example) along an equaliser bar 18 (as used eg, on vehicle rear-brake systems) so that the bar is free to swivel about the end of rod 17. A rod 19 (the aforesaid first rod) connects a pin at the upper end of bar 18 to a pin located towards the upper edge of one of the plates 3 of the index finger shown in FIG. 2, and is free to swivel about both pins. A rod 20 (the aforesaid second rod) similarly connects a pin at the lowr end of bar 18 to a triangular crank 21 pivotted at 22 on the base 1, and a rod 23 (the aforesaid third rod) similarly connects the crank 21 to a pin on one of the plates 5 of the index finger. The rod 23 is pivotted on crank 21 at 35 (hidden in FIG. 1), pivots 4 and 35 being substantially co-linear (but separate) when the finger is straight.

The above-described arrangement operates as follows. As shown, the index finger 2 is fully extended, with the cross-head 15 at the right-hand end of its travel. If now the motor 11 is energised so that the cross-head is moved towards the left by rod 13, the equaliser bar 18 is pulled leftwards by the rod 17. The rods 19 and 20 thereby exert a pull on the bars 3 and crank 21 respectively, but, primarily because of the geometry of the arrangement, there is a greater mechanical advantage via the bar 19 than via the bar 20 (the perpendicular distance from pivot 22 to the axis of bar 20 being less than the equivalent distance from pivot 4 to bar 19). By the known action of the equaliser bar 18, the finger therefore remains straight but rotates upwards about the pivots 4 of the lower section. If now the upward movement of the lower finger-section, ie, the plates 3, is stopped or strongly resisted by meeting an object such as bar 25 shown in section, the action of the equaliser bar 18 is to transfer the pull to rod 20 which, via the crank 21, is transmitted to rod 23 thereby causing the middle finger-section, ie, the plates 5, to rotate about the pivots 6, and the tip-section, ie, the member 7, to rotate simultaneously about the pivots 8. The three finger-portions thus close round the bar 25 and grip it.

If the bar 25 is free to move thereafter, albeit presenting a load, eg, its weight, and the motor drive is maintained, the pull will transfer back to rod 19 and the upward movement of the now-closed finger will continue, eventually reaching, if allowed, the final position shown at 26. (Normally the finger will be covered by the glove 10 in the present application). The final positions of rod 9 and 23 are indicated by interrupted lines. It will be seen that the action of the finger 2 thus closely simulates that of a human finger, in which the middle and tip sections likewise naturally bend simultaneously.

In the hand shown, the other three fingers 2 are operated simultaneously, but independently of the index finger, by a similar mechanism applied to the "little finger" and shown in FIGS. 1 and 3 with corresponding numerals primed. FIG. 3 shows how the crank 21' is coupled via shafts 27 and 28 to cranks 29 connected to the respective rods 23" of the two middle fingers. As in a human hand, the pivots 4' of the little finger are set slightly behind those of the other three fingers, requiring an additional small connecting rod 30 between a crank 31 on shaft 27 and the adjacent crank 29 on shaft 28. (If other finger pivots are similarly staggered for particular applications, another rod or rods 30 is required).

A third motor 32, encoder and reduction gearing is provided for rotating a "thumb" (not shown). In this example the thumb is jointless and pivotted only at its lower end, but slightly bent. Its pivot is so located relative to the pivots 4 of the index finger as to allow objects to be picked up between their respective tips.

Although the action of the fingers depends primarily on the difference between the mechanical advantage obtained via rods 19 and 20 as a result of the geometry of the arrangement, particularly the larger turning movement about pivot 4 via rod 19 than about pivot 6 via rod 20, crank 21 and rod 23, a part is also played by the greater frictional forces present in the latter case and also by the stiffness of the glove in which the fingers are inserted. It may thus be necessary to "tune" the hand for optimum performance and one adjustment that can be made for this purpose is the point of attachment of rod 17 to equaliser bar 18, which can be varied along the bar. (In applications where no glove is used, such stiffness can be provided by adding springs (not shown) to the mechanism).

In the above-described hand the driving means is provided by rotary electric motors. Alternatively, linear actuators may be used, eg, connected directly to the cross-head 15; the actuators may be electric, hydraulic or pneumatic.

The present gripping device can take forms other than simulating a human finger, nor need it be part of a simulated human hand. For example, it may comprise only two finger sections instead of three, the upper finger section of the two being itself rigid but, for example, bent to allow an object to be gripped between it and the lower section. The device may also comprise more than three individually rotable sections, the fourth being coupled to the third by a rod corresponding to rod 9, and so on for any further sections. The thumb of a simulated hand may comprise a two-section form of the present device instead of being rigid as in the described hand.

We claim:

1. A gripping device comprising:
   a lower finger-section pivotted at its lower end to a base and at least a first upper finger-section pivotted to the lower section;
   a driving means mounted on said base for driving said finger-section;
   and linkage means between said driving means and said finger-sections for preferentially rotating said lower finger-section about its pivot, said linkage means being arranged so that, upon rotation of said lower finger-section being stopped or strongly resisted by an object to be gripped, the drive transfers to said first upper finger-section causing it to rotate about its pivot towards the lower finger-section and thereby tend to grip the object between said finger-sections.

2. A device as claimed in claim 1 wherein the linkage means comprises an equaliser bar having an intermediate point linearly moveable by said driving means and having a first rod linking one end of the bar to the lower finger-section and a second rod linking the other end of the bar to a crank pivotted on said base, said crank being linked to the first upper finger-section by a third rod, said linkage means being arranged such that the mechanical advantage obtained via the second rod is substantially less than that obtained via the first rod whereby to cause said initial preferential rotation of the lower finger-section.

3. A device as claimed in claim 1, closely simulating the action of a human finger, wherein there is provided a second upper finger-section pivotted to said first upper finger-section and linkage means between said first and second upper finger-sections whereby rotation of said first upper finger-section about its pivot causes rotation of said second upper finger-section about its pivot.

4. A robotic hand comprising four devices as claimed in claim 3 pivoted to a common base and simulating the action of the four human fingers, including an index finger.

5. A hand as claimed in claim 4 wherein the index finger comprises one said gripping device operable via one said linkage by one said driving means and the other three fingers comprise three of said gripping devices coupled together to be operable simultaneously, but independently of the index finger, via a second said linkage by a second said driving means.

6. A device as claimed in claim 1 wherein the driving means comprises at least one rotary electric motor.

7. A device as claimed in claim 2, closely simulating the action of a human finger, wherein there is provided a second upper finger-section pivoted to said first upper finger-section and linkage means between said first and second upper finger-sections whereby rotation of said first upper finger-section about its pivot causes rotation of said second upper finger-section about its pivot.

8. A robotic hand comprising four devices as claimed in claim 7 pivoted to a common base and simulating the action of the four human fingers, including an index finger.

9. A hand as claimed in claim 8 wherein the index finger comprises one said gripping device operable via one said linkage by one said driving means and the other three fingers comprise three of said gripping devices coupled together to be operable simultaneously, but independently of the index finger, via a second said linkage by a second said driving means.

* * * * *